(12) United States Patent
Curley

(10) Patent No.: US 9,033,972 B2
(45) Date of Patent: May 19, 2015

(54) METHODS AND DEVICES FOR FLUID ENHANCED MICROWAVE ABLATION THERAPY

(71) Applicant: Thermedical, Inc., Waltham, MA (US)

(72) Inventor: Michael G. Curley, Weston, MA (US)

(73) Assignee: Thermedical, Inc., Waltham, MA (US)

( * ) Notice: Subject to any disclaimer, the term of this patent is extended or adjusted under 35 U.S.C. 154(b) by 0 days.

(21) Appl. No.: 13/837,295

(22) Filed: Mar. 15, 2013

(65) Prior Publication Data

US 2014/0276743 A1 Sep. 18, 2014

(51) Int. Cl.
*A61B 18/18* (2006.01)
*A61B 18/00* (2006.01)
*A61B 18/04* (2006.01)

(52) U.S. Cl.
CPC ... *A61B 18/1815* (2013.01); *A61B 2018/00017* (2013.01); *A61B 2018/00029* (2013.01); *A61B 2018/00351* (2013.01); *A61B 2018/00529* (2013.01); *A61B 2018/00577* (2013.01); *A61B 2018/00642* (2013.01); *A61B 2018/0066* (2013.01); *A61B 2018/00702* (2013.01); *A61B 2018/00714* (2013.01); *A61B 2018/00821* (2013.01); *A61B 2018/00898* (2013.01); *A61B 2018/00011* (2013.01); *A61B 2018/044* (2013.01)

(58) Field of Classification Search
USPC ........................................ 606/27, 33, 41, 414
See application file for complete search history.

(56) References Cited

U.S. PATENT DOCUMENTS

| | | | |
|---|---|---|---|
| 4,160,455 | A | 7/1979 | Law |
| 4,424,190 | A | 1/1984 | Mather, III et al. |
| 5,336,222 | A | 8/1994 | Durgin, Jr. et al. |
| 5,403,311 | A | 4/1995 | Abele et al. |
| 5,431,648 | A | 7/1995 | Lev |
| 5,431,649 | A | 7/1995 | Mulier et al. |
| 5,449,380 | A | 9/1995 | Chin |

(Continued)

FOREIGN PATENT DOCUMENTS

| | | |
|---|---|---|
| EP | 0 895 756 A1 | 2/1999 |
| EP | 0 908 156 A1 | 4/1999 |

(Continued)

OTHER PUBLICATIONS

Brace CL. Microwave tissue ablation: biophysics, technology, and applications.; Crit Rev Biomed Eng. 2010;38(1):65-78.

(Continued)

*Primary Examiner* — Michael Peffley
*Assistant Examiner* — Daniel Fowler
(74) *Attorney, Agent, or Firm* — Nutter McClennen & Fish LLP; Ronald E. Cahill; Derek P. Roller

(57) ABSTRACT

Devices and methods for fluid enhanced ablation therapy using microwave antennas are described herein that provide improved heat transfer into a target volume of tissue and improved antenna cooling compared to prior art designs. In one embodiment, fluid can be introduced into a target volume of tissue along with the delivery of therapeutic energy from a microwave antenna positioned within the target volume of tissue. The fluid can become heated by cooling the microwave antenna and, if additional heating of the fluid is desired, a heating element disposed within the microwave antenna can supplementally heat the fluid prior to introduction into the target volume of tissue.

10 Claims, 13 Drawing Sheets

(56) References Cited

U.S. PATENT DOCUMENTS

| | | | |
|---|---|---|---|
| 5,462,521 A * | 10/1995 | Brucker et al. | 604/20 |
| 5,472,441 A | 12/1995 | Edwards et al. | |
| 5,496,271 A * | 3/1996 | Burton et al. | 607/27 |
| 5,522,815 A | 6/1996 | Durgin, Jr. et al. | |
| 5,545,195 A | 8/1996 | Lennox et al. | |
| 5,549,559 A | 8/1996 | Eshel | |
| 5,653,692 A | 8/1997 | Masterson et al. | |
| 5,728,143 A | 3/1998 | Gough et al. | |
| 5,800,482 A | 9/1998 | Pomeranz et al. | |
| 5,827,269 A | 10/1998 | Saadat | |
| 5,891,094 A | 4/1999 | Masterson et al. | |
| 5,891,134 A | 4/1999 | Goble et al. | |
| 5,954,719 A | 9/1999 | Chen et al. | |
| 6,024,743 A | 2/2000 | Edwards | |
| 6,030,379 A * | 2/2000 | Panescu et al. | 606/34 |
| 6,032,077 A | 2/2000 | Pomeranz | |
| 6,045,549 A | 4/2000 | Smethers et al. | |
| 6,056,746 A | 5/2000 | Goble et al. | |
| 6,112,123 A | 8/2000 | Kelleher et al. | |
| 6,119,041 A | 9/2000 | Pomeranz et al. | |
| 6,139,570 A | 10/2000 | Saadat et al. | |
| 6,139,571 A | 10/2000 | Fuller et al. | |
| 6,179,803 B1 * | 1/2001 | Edwards et al. | 604/22 |
| 6,208,881 B1 | 3/2001 | Champeau | |
| 6,233,490 B1 * | 5/2001 | Kasevich | 607/101 |
| 6,272,370 B1 | 8/2001 | Gillies et al. | |
| 6,302,904 B1 | 10/2001 | Wallsten et al. | |
| 6,328,735 B1 | 12/2001 | Curley et al. | |
| 6,358,273 B1 | 3/2002 | Strul et al. | |
| 6,443,947 B1 | 9/2002 | Marko et al. | |
| 6,463,332 B1 | 10/2002 | Aldrich | |
| 6,468,274 B1 | 10/2002 | Alleyne et al. | |
| 6,529,756 B1 | 3/2003 | Phan et al. | |
| 6,565,561 B1 | 5/2003 | Goble et al. | |
| 6,620,155 B2 | 9/2003 | Underwood et al. | |
| 6,641,580 B1 | 11/2003 | Edwards et al. | |
| 6,702,810 B2 | 3/2004 | McClurken et al. | |
| 6,752,802 B1 | 6/2004 | Isenberg et al. | |
| 6,772,012 B2 | 8/2004 | Ricart et al. | |
| 6,814,730 B2 | 11/2004 | Li | |
| 6,904,303 B2 | 6/2005 | Phan et al. | |
| 6,972,014 B2 | 12/2005 | Eum et al. | |
| 7,001,378 B2 | 2/2006 | Yon et al. | |
| 7,070,597 B2 | 7/2006 | Truckai et al. | |
| 7,101,369 B2 | 9/2006 | van der Welde | |
| 7,207,989 B2 | 4/2007 | Pike, Jr. et al. | |
| 7,244,254 B2 | 7/2007 | Brace et al. | |
| 7,270,659 B2 | 9/2007 | Ricart et al. | |
| 7,311,703 B2 * | 12/2007 | Turovskiy et al. | 606/33 |
| 7,387,625 B2 | 6/2008 | Hovda et al. | |
| 7,604,634 B2 | 10/2009 | Hooven | |
| 7,879,030 B2 | 2/2011 | Paul et al. | |
| 7,938,822 B1 * | 5/2011 | Berzak et al. | 606/20 |
| 7,951,143 B2 | 5/2011 | Wang et al. | |
| 7,993,335 B2 | 8/2011 | Rioux et al. | |
| 8,128,620 B2 | 3/2012 | Wang et al. | |
| 8,128,621 B2 | 3/2012 | Wang et al. | |
| 8,273,082 B2 | 9/2012 | Wang et al. | |
| 8,439,907 B2 * | 5/2013 | Auth et al. | 606/33 |
| 8,702,697 B2 | 4/2014 | Curley | |
| 2001/0031946 A1 | 10/2001 | Walker et al. | |
| 2002/0120259 A1 | 8/2002 | Lettice et al. | |
| 2002/0183735 A1 | 12/2002 | Edwards et al. | |
| 2003/0109871 A1 * | 6/2003 | Johnson et al. | 606/42 |
| 2004/0006336 A1 | 1/2004 | Swanson | |
| 2004/0220559 A1 | 11/2004 | Kramer et al. | |
| 2004/0230190 A1 | 11/2004 | Dahla et al. | |
| 2005/0015081 A1 | 1/2005 | Turovskiy et al. | |
| 2005/0055019 A1 | 3/2005 | Skarda | |
| 2005/0165391 A1 | 7/2005 | Maguire et al. | |
| 2005/0192652 A1 | 9/2005 | Cioanta et al. | |
| 2005/0245923 A1 | 11/2005 | Christopherson et al. | |
| 2006/0085054 A1 | 4/2006 | Zikorus et al. | |
| 2006/0118127 A1 | 6/2006 | Chinn | |
| 2006/0216275 A1 | 9/2006 | Mon | |
| 2006/0259024 A1 | 11/2006 | Turovskiy et al. | |
| 2006/0276780 A1 * | 12/2006 | Brace et al. | 606/33 |
| 2007/0032786 A1 | 2/2007 | Francischelli | |
| 2007/0219434 A1 | 9/2007 | Abreu | |
| 2007/0287998 A1 | 12/2007 | Sharareh et al. | |
| 2007/0288075 A1 | 12/2007 | Dowlatshahi | |
| 2008/0086073 A1 | 4/2008 | McDaniel | |
| 2008/0161797 A1 | 7/2008 | Wang et al. | |
| 2008/0167650 A1 | 7/2008 | Joshi et al. | |
| 2009/0069808 A1 | 3/2009 | Pike, Jr. et al. | |
| 2009/0082837 A1 | 3/2009 | Gellman et al. | |
| 2009/0093811 A1 * | 4/2009 | Koblish et al. | 606/41 |
| 2009/0118725 A1 * | 5/2009 | Auth et al. | 606/33 |
| 2009/0118727 A1 | 5/2009 | Pearson et al. | |
| 2009/0163836 A1 | 6/2009 | Sliwa | |
| 2009/0254083 A1 * | 10/2009 | Wallace et al. | 606/41 |
| 2010/0094272 A1 | 4/2010 | Rossetto et al. | |
| 2010/0198056 A1 | 8/2010 | Fabro et al. | |
| 2010/0292766 A1 | 11/2010 | Duong et al. | |
| 2010/0324471 A1 | 12/2010 | Flaherty et al. | |
| 2011/0137150 A1 | 6/2011 | Connor et al. | |
| 2012/0108938 A1 | 5/2012 | Kauphusman et al. | |
| 2012/0265190 A1 | 10/2012 | Curley et al. | |
| 2012/0265199 A1 | 10/2012 | Curley | |
| 2012/0265200 A1 | 10/2012 | Curley | |
| 2012/0265276 A1 | 10/2012 | Curley | |
| 2012/0277737 A1 | 11/2012 | Curley | |
| 2012/0310230 A1 | 12/2012 | Willis | |
| 2014/0052117 A1 | 2/2014 | Curley | |
| 2014/0188106 A1 | 7/2014 | Curley | |
| 2014/0275977 A1 | 9/2014 | Curley et al. | |

FOREIGN PATENT DOCUMENTS

| | | |
|---|---|---|
| EP | 1 033 107 A1 | 9/2000 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2010/002733 A1 | 1/2010 |
| WO | 2010/151619 A2 | 12/2010 |
| WO | 2012/071058 A1 | 5/2012 |

OTHER PUBLICATIONS

David R. Lide (ed)., CRC Handbook of Chemistry and Physics, 87th Edition. 2006. p. 8-81. CRC Press, Florida.

International Search Report and Written Opinion for Application No. PCT/US2012/033203, issued Sep. 21, 2012. (23 pages).

International Search Report and Written Opinion for Application No. PCT/US2012/033213, issued Sep. 21, 2012. (17 pages).

International Search Report and Written Opinion for Application No. PCT/US2012/033216, issued Sep. 21, 2012. (17 pages).

International Search Report and Written Opinion for Application No. PCT/US2012/033327, issued Sep. 21, 2012. (14 pages).

International Search Report and Written Opinion for Application No. PCT/US2012/033332, issued Sep. 21, 2012. (20 pages).

Nath et al., Prog. Card. Dis. 37(4):185-205 (1995).

Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.

Sapareto et al., Int. J Rad. One. Biol. Phys. 10(6):787-800 (1984).

International Search Report and Written Opinion for Application No. PCT/US2013/053977, issued Nov. 14, 2013. (20 pages).

International Search Report and Written Opinion for Application No. PCT/US2014/024731, mailed Jul. 21, 2014 (39 pages).

Extended European Search Report and Written Opinion for Application No. 12771601.7 issued Oct. 27, 2014 (7 pages).

(56) References Cited

OTHER PUBLICATIONS

Extended Search Report and Written Opinion for EP 12 77 0537 dated Oct. 10, 2014 (6 pages).
Extended Search Report and Written Opinion for EP 12 77 0631.5 dated Oct. 1, 2014 (6 Pages).
Extended Search Report and Written Opinion for EP 12 77 1331.1 dated Sep. 25, 2014 (6 Pages).
Extended Search Report and Written Opinion for EP 12 77 1876 dated Oct. 13, 2014 (6 pages).

* cited by examiner

METHODS AND DEVICES FOR FLUID ENHANCED MICROWAVE ABLATION THERAPY

FIELD

The present invention relates generally to fluid enhanced ablation therapy, and more particularly, to devices and methods for conducting fluid enhanced ablation therapy using microwave antennas.

BACKGROUND

Ablation therapy uses heat to kill undesirable tissue. Energy from various sources, often radiofrequency (RF) electrical energy, but also microwave, ultrasound, or laser energy, is used to heat tissue to a therapeutic temperature and thereby kill the tissue. This therapy can be used to treat various small tumors, including malignant tumors such as liver cancer or benign tumors such as uterine fibroids, by overheating and killing the tumorous tissue. It can also be used to ablate arrhythmogenic heart tissue that causes arrhythmias, such as atrial flutter. While ablation therapy is often used to treat small amounts of tissue such as those mentioned above, conducting the therapy for larger tumors, or for other conditions that require treating large volumes of tissue, remains difficult.

One prior art solution for ablating larger volumes of tissue has been the use of microwave energy in place of RF electrical energy. Microwave energy can be better suited for use in large treatment volumes because its energy can penetrate farther into tissue than RF energy. For example, microwave energy at 915 MHz can penetrate approximately 4 cm (in theory) into tissue, as compared to RF energy that is typically dissipated beyond about 1 cm from the electrodes that deliver the energy. Therefore, microwave energy can directly heat a greater volume of tissue than RF energy.

Microwave energy can have additional advantages over other energy sources as well. For example, microwaves propagate through all types of tissues and non-metallic materials, including charred and desiccated tissues that can be created during the ablative process. In contrast, when tissue becomes charred or desiccated by RF ablation the impedance of the tissue rises dramatically, making it difficult to pass further current through the tissue and effectively terminating the therapy. Still further, microwaves can deliver greater levels of direct heating energy as compared to other ablation energies, which can be advantageous when ablation is conducted in organs with high blood perfusion or near sources of blood flow, such as veins or arteries, that can draw heat away from a target tissue volume.

However, microwave energy does have drawbacks as well. For example, while the depth of treatment may extend farther into tissue than with RF energy, it is still limited. As mentioned above, in theory the field is typically dissipated at about 4 cm from the microwave antenna. In practice, the cylindrical configuration of microwave antenna exacerbate the radial spreading of that energy into tissue being treated, resulting in dissipation within 2 cm of the cylindrical antenna. Treating larger volumes of tissue therefore requires repositioning the antenna or using multi-antenna arrays. Further, the dynamics of the microwave field can become complex when multi-antenna arrays are used. As a result, therapy procedure times and costs can be significantly increased due to either repositioning a single probe several times or setting up a multi-antenna array.

In addition, the microwave energy deposition field is static and is defined by the electromagnetic properties of the surrounding tissues and the geometry of the antenna itself. Within the heating field there are volumes of tissue that are heated more or less than others (e.g., similar to reheating food in a microwave oven). This can lead to undesirable therapies, as some tissue can be heated to a dangerous level by a strong microwave field (e.g., becoming superheated and explosively converting to steam), while other tissue can be heated to a sub-therapeutic temperature by a weaker microwave field. Thermal energy does flow from the volumes of tissue that are heated by strong microwave fields to those heated by weaker microwave fields by thermal conduction, but this is a slow and inefficient process in tissue, and does not address the safety concern created by superheating portions of a target volume of tissue.

Moreover, microwave energy can overheat the antenna used for therapy application and its associated cabling used to transfer power to the antenna from a generator. This internal heating must be countered by limiting energy transmission or by actively cooling the components of the microwave ablation system to prevent undesired thermal damage to tissues in contact with the antenna or the cabling extending to the antenna. Prior art methods for actively cooling microwave antennas include circulating a fluid or cryogenic gas along the length of the cable and even through the antenna itself, but these closed-loop systems can result in large diameter devices, e.g., due to the need for delivery and return lumens.

Accordingly, there is a need for improved devices and methods for conducting ablation using microwave antennas. In particular, there is a need for microwave ablation devices and methods that can deliver therapeutic doses of thermal energy to large volumes of tissue and address cooling issues commonly encountered with microwave antennas.

SUMMARY

The present invention generally provides devices and methods for using microwave antennas in combination with fluid enhanced ablation therapy. For example, the methods described herein generally include placing a microwave antenna within a target volume of tissue and simultaneously delivering microwave electrical energy and a fluid into the tissue. The fluid introduced into the tissue can aid in distributing the heat from the microwave field throughout the tissue volume via convection. Furthermore, in some embodiments, the fluid itself can be heated to a therapeutic level prior to being introduced into the tissue. Accordingly, the fluid can act as a therapeutic agent and the energy delivered through the microwave antenna can replenish heat lost from the fluid into the target tissue volume.

In addition to utilizing the fluid as a therapeutic agent to ablate larger volumes of tissue, the devices and methods described herein can also utilize the fluid to aid in cooling the microwave antenna or cabling extending between a power generator and the microwave antenna. Indeed, in some embodiments, excess heat from the microwave antenna and/or its associated cabling can be used to at least partially heat the fluid to a therapeutic temperature before introducing the fluid into the target volume of tissue, thereby putting traditionally wasted heat to use in the therapy. Still further, in embodiments in which a cryogenic gas is utilized to cool the antenna and/or associated cabling, a heating element disposed within a fluid passageway can be used in combination with the cooling action of the cryogenic gas to deliver fluid at any temperature (e.g., any temperature above freezing) into the target volume of tissue.

In one aspect, a microwave ablation device is provided that includes an elongate body having an inner conducting element surrounded by a dielectric insulator, an outer conducting element coaxially disposed around the dielectric insulator and defining an outer wall, and at least one fluid channel extending through the elongate body parallel to a longitudinal axis of the microwave antenna. The at least one fluid channel can include at least one opening to allow fluid to flow into tissue surrounding the elongate body, and the inner and outer conducting elements can be configured to deliver microwave energy to tissue surrounding the elongate body.

The devices and methods described herein can include a variety of additional features or modifications, all of which are considered within the scope of the present invention. For example, in some embodiments the microwave antenna can have a cylindrical shape, and the inner conducting element, dielectric insulator, and outer conducting element can be coaxially aligned. In other embodiments, the device can further include a shield disposed around and coaxially aligned with the outer conducting element.

In other embodiments, the at least one opening can be positioned at a location proximal to a distal end of the inner conductive element. The at least one opening can, in some embodiments, include a plurality of openings. The plurality of openings can be spaced circumferentially around a longitudinal axis of the at least one fluid channel, and/or they can be spaced along a longitudinal axis of the at least one fluid channel.

The at least one fluid channel can, in some embodiments, extend through the dielectric insulator between the inner conducting element and the outer conducting element, and the at least one opening can extend through the outer conducting element. Furthermore, in certain embodiments, the at least one fluid channel can include a heating element disposed therein. The heating element can be positioned proximal to the at least one opening and configured to heat fluid flowing through the channel.

In another aspect, an ablation device is provided that includes at least one elongate body having proximal and distal ends and at least one microwave antenna extending from a distal end of the at least one elongate body. The at least one microwave antenna can have an arced shape that defines a plane, and the device can further include a fluid channel extending through one of the body(s) and configured to deliver fluid into tissue from a center point of the arc defined by the microwave antenna. The fluid channel can also include a heating element disposed therein and configured to heat fluid flowing through the channel.

In some embodiments, the device includes first and second elongate bodies and first and second microwave antennas, with the first microwave antenna extending from the distal end of the first elongate body and the second microwave antenna extending from the distal end of the second elongate body. The planes of the arc shaped antennas can be angularly offset from one another such that the first and second microwave antennas generally define a sphere.

In another aspect, an ablation device is provided that includes a microwave antenna having a hollow outer conducting element, a coaxial inner conducting element extending through the outer conducting element, a fluid channel positioned between the outer and inner conducting elements, an inner lumen extending through the inner conducting element, and at least one outlet port formed in the outer conducting element and in fluid communication with the fluid channel. The at least one outlet port can be configured to deliver fluid flowing through the fluid channel into tissue surrounding the microwave antenna. The inner lumen can be configured to receive a cryogenic gas source. The fluid channel can also include at least one heating element disposed therein and configured to heat fluid flowing through the channel.

In still another aspect, a method for ablating tissue is provided that includes delivering therapeutic energy through a microwave antenna configured to be positioned within a volume of tissue, and simultaneously delivering heated fluid into the volume of tissue through at least one outlet port formed in the microwave antenna, wherein the fluid is heated by contact with the microwave antenna.

In some embodiments, heating the fluid by contact with the microwave antenna can have the additional benefit of cooling the antenna to prevent overheating. As a result, heat that is traditionally wasted can be utilized in the therapy. If the fluid is not heated sufficiently by contacting the microwave antenna, the method can further include raising the temperature of the heated fluid prior to introduction into the volume of tissue using at least one heating element disposed within the microwave antenna. In certain exemplary embodiments, the heated fluid has a heat capacity that is equal to or greater than 2 J/ml-° C. (about ½ the heat capacity of tissue).

In another aspect, a method for ablating tissue is provided that includes delivering therapeutic energy into a volume of tissue using a microwave antenna, and cooling the microwave antenna by delivering a cryogenic gas through at least one gas channel formed in the microwave antenna. The method also includes delivering a fluid into the volume of tissue through at least one fluid channel formed in the microwave antenna, and controlling the temperature of the fluid delivered into the volume of tissue using the cooling of the cryogenic gas and a heating element disposed within the at least one fluid channel. By balancing the cooling effects of the cryogenic gas with the output of the heating element, fluid of almost any desired temperature can be introduced into the volume of tissue. In certain embodiments, for example, the temperature of the fluid delivered into the volume of tissue can be controlled to be between a freezing temperature of the fluid and a temperature of the volume of tissue.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1:
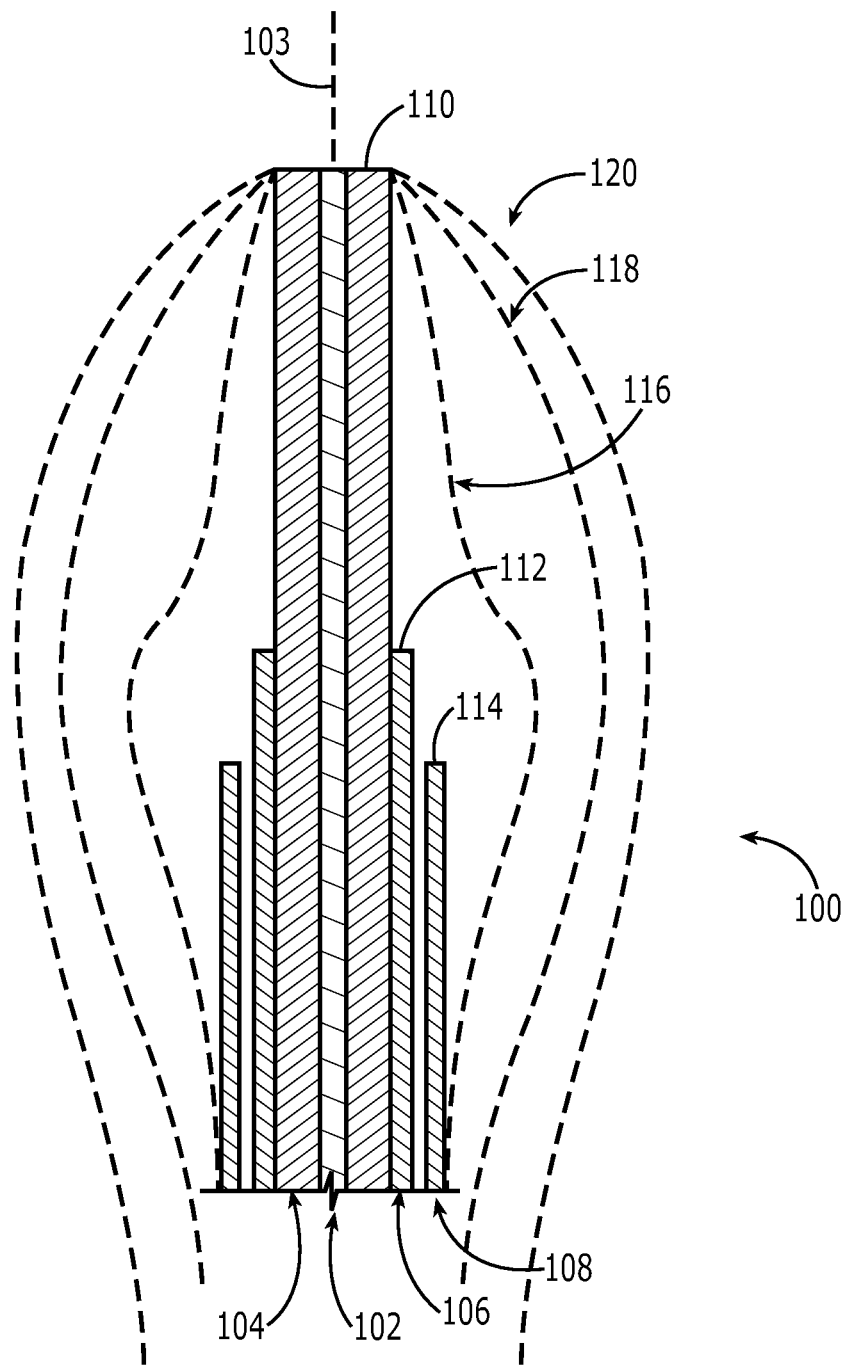
FIG. 1 is a cross-sectional diagram of a prior art microwave antenna.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to devices and methods for fluid enhanced ablation therapy using microwave antennas. As mentioned above, the devices and methods described herein generally include placing a microwave antenna within a target volume of tissue and simultaneously delivering microwave electrical energy and a fluid into the tissue. The fluid introduced into the tissue can aid in distributing the heat from the microwave field throughout the tissue volume via convection. Furthermore, in some embodiments, the fluid itself can be heated to a therapeutic level prior to being introduced into the tissue. Accordingly, the fluid can act as a therapeutic agent and the energy delivered through the microwave antenna can replenish heat lost from the fluid into the target tissue volume. The introduction of fluid into the volume of tissue in combination with the microwave field can effectively destroy tissue far beyond the approximately 2 cm practical limit of conventional microwave antennas, and even well beyond the 4 cm theoretical limit of conventional microwave antennas mentioned above. Further, the devices and methods described herein can allow for treating large volumes of tissue with a single probe in a single position, thereby reducing therapy time and cost. Of course, the devices and methods described herein can also be applied to microwave antenna architectures that utilize multiple probes.

Moreover, the devices and methods described herein can provide enhanced cooling to a microwave antenna or cabling extending between a power generator and the microwave antenna. Further, the excess heat drawn from the microwave antenna can raise the temperature of the fluid prior to its introduction into the target volume of tissue, thereby putting heat that is typically wasted to use in the therapy. The heat from the microwave antenna alone can be used to heat the fluid, or the fluid can be supplementally heated by a heating element prior to being introduced into the target volume of tissue. Still further, in embodiments in which a cryogenic gas is used to cool the microwave antenna and/or its cabling, a balance of the cooling effects of the cryogenic gas and the output power of a heating element can be used to provide fluid at any desired temperature—even temperatures below room or body temperature.

FIG. 1 illustrates one embodiment of a prior art microwave antenna 100 and its associated microwave field shape and strength at various distances from the antenna. The antenna 100 is a triaxial architecture in a 17 gauge probe, as described by Brace, CL *Crit Rev Biomed Eng.* 2010; 38(1): 65-78. The triaxial antenna 100 is a generally cylindrical antenna having a central inner conductor 102, such as an active electrode, extending along a longitudinal axis 103 thereof. The inner conductor 102 can be surrounded by a dielectric insulator 104 that is coaxially aligned with, and extends over an outer surface of, the inner conductor. Extending over an outer surface of the dielectric insulator 104 can be an outer conductor 106, such as a return electrode. In addition, a shield 108 can extend over an outer surface of the outer conductor 106.

The various components of the microwave antenna 100 can extend for different lengths along the longitudinal axis 103 of the antenna. For example, the inner conductor 102 and the dielectric insulator 104 can extend along the entire length of the antenna 100, and the inner conductor 102 can be exposed at a distal end 110 thereof. The outer conductor 106 can extend to a first endpoint 112 that is proximal to the distal end 110, and the shield 108 can extend to a second endpoint 114 that is proximal to the first endpoint 112. This arrangement leaves specific sidewall portions of the inner and outer conductors 104, 106 exposed and results in a tear-drop shaped microwave field formed around the antenna 100, as shown by field-strength lines 116, 118, 120.

As can be seen in the figure, the microwave field strength is strongest (e.g., 800 V/m) along the field strength line 116 that is closest to the antenna 100. The field strength dissipates with distance from the antenna 100, as shown by field strength lines 118 (e.g., 600 V/m) and 120 (e.g., 200 V/m). In particular, the field strength can be greatest within about 4 mm of the antenna 100, and can fall to negligible levels by about 1 cm from the antenna.

Thermal conduction can serve to treat volumes of tissue extending farther than 1 cm from the antenna 100, as heat can flow from the tissue heated directly by the microwave field into tissue that is unheated due to the thermal gradients that result from the non-uniform field. As mentioned above, however, it is accepted that the treatment field from a single antenna 100 is limited to a distance of about 4 cm, and more practically about 2 cm, from the antenna. Treating larger volumes of tissue can require the use of additional microwave antennas, or the subsequent repositioning of the antenna 100 in various portions of the larger volume to be treated. Using additional antennas can be challenging and often adds significant time to the therapy because the desired relative placements of the multiple antennae can be difficult to achieve and because the resulting microwave field can be difficult to monitor.

The devices and methods of the present invention can utilize fluid enhanced ablation therapy to address these challenges. Fluid enhanced ablation therapy, as mentioned above, is defined by passing a fluid into tissue while delivering therapeutic energy from an ablation element. The delivery of therapeutic energy into tissue causes hyperthermia in the tissue, ultimately resulting in necrosis. A variety of fluids can be used to conduct the therapy. In some embodiments, a sterile normal saline solution (defined as a salt-containing solution) can be utilized. However, other liquids may be used, including sterile water, Ringer's solution, or concentrated saline solution. A fluid can be selected to provide the desired therapeutic and physical properties when applied to the target tissue and a sterile fluid is recommended to guard against infection of the tissue. In an exemplary embodiment, the fluid has a heat capacity that is substantially the same as or greater than the heat capacity of tissue such that, as the fluid is delivery to the target tissue, the fluid can retain its temperature as heat is exchanged with the tissue. For example, the fluid can have a heat capacity of greater than about 4 J/ml-° C., and more preferably greater than about 2 J/ml-° C. (which is about ½ the heat capacity of tissue).

One example of fluid enhanced ablation therapy is the SERF™ ablation technique (Saline Enhanced Radio Frequency™ ablation) described in U.S. Pat. No. 6,328,735, which is hereby incorporated by reference in its entirety. The SERF ablation technique delivers fluid heated to a therapeutic temperature into tissue along with RF energy. Delivering heated fluid in combination with microwave power can enhance the ablation treatment because the fluid flow through the extracellular space of the treatment tissue can increase the heat transfer through the tissue significantly. The flowing heated fluid can convect thermal energy from the antenna farther into the target tissue. In addition, the fact that the fluid is heated to a therapeutic temperature increases the amount of energy that can be imparted into the tissue.

An advantage of fluid enhanced ablation therapy is that the use of flowing saline can avoid overheating the tissue located adjacent to the microwave antenna because the heat cannot be efficiently transported away from the antenna. During fluid enhanced ablation therapy, the therapeutically heated fluid can convect heat deeper into the target tissue, thereby reducing tissue charring near to the antenna. Further, because the fluid is heated to a therapeutic level, it does not act as a heat sink that draws down the temperature of the surrounding tissue. Therefore, the total volume of tissue that can be heated to therapeutic temperatures is increased. For example, experimental testing using RF electrical energy has demonstrated that a volume of tissue having a diameter of approximately 8 cm (i.e., a spherical volume of approximately 156 cm$^3$) can be treated in 5 minutes using fluid enhanced ablation therapy techniques.

In addition, fluid enhanced ablation therapy devices have a greater number of parameters that can be varied to adjust the shape of the treatment profile according to the tissue being treated. For example, operators or control systems can modify parameters such as saline temperature (e.g., from about 40° C. to about 80° C.), saline flow rate (e.g., from about 0 ml/min to about 20 ml/min), output power (e.g., from about 0 W to about 200 W), and duration of treatment (e.g., from about 0 min to about 10 min) to adjust the temperature profile within the target volume of tissue.

Figure 2:
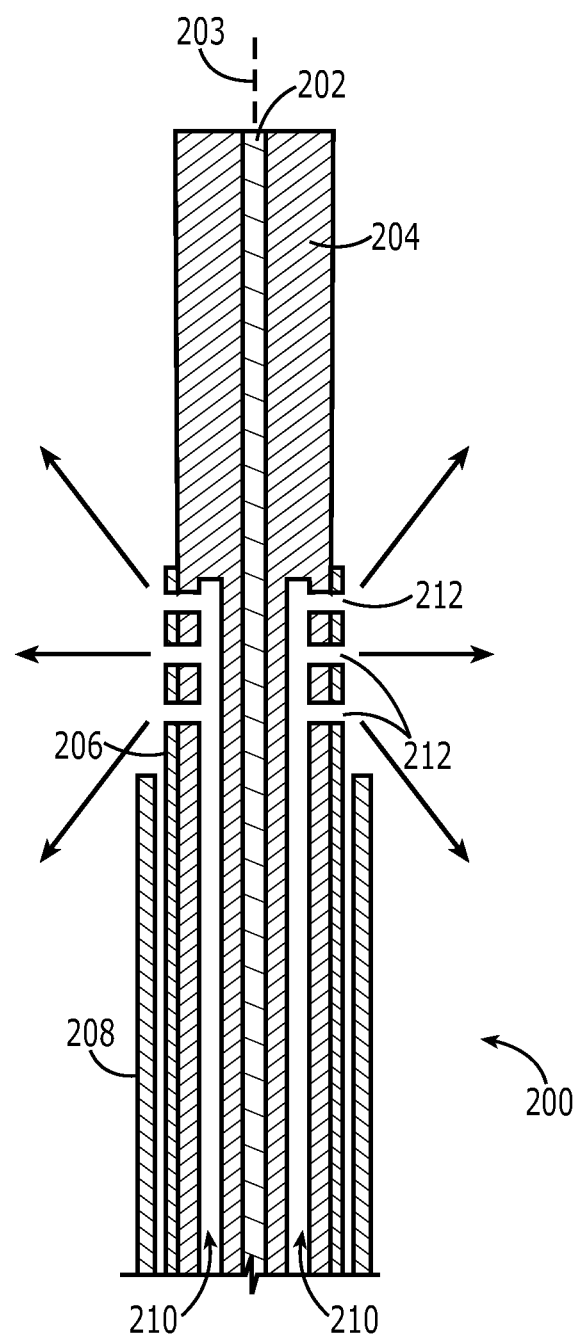
FIG. 2 is a cross-sectional diagram of one embodiment of a microwave antenna.

FIG. 2 illustrates one embodiment of a microwave antenna 200 that can be used in fluid enhanced ablation therapy. The antenna 200 shares the triaxial architecture of the antenna 100 discussed above, including an inner conductor 202, dielectric insulator 204, outer conductor 206, and shield 208 extending along a length thereof. The antenna can have a variety of sizes according to its intended use (e.g., laparoscopic treatment of the liver, catheter-based treatment of the heart, etc.), the size of the target tissue volume, etc. In one embodiment, the microwave antenna can be mounted on a 17 gauge probe having an outer diameter of approximately 1.5 mm and a length of about 20 cm.

To facilitate its use in fluid enhanced ablation therapy techniques, the antenna 200 can include at least one fluid channel formed therein to deliver fluid into tissue surrounding the antenna. In the illustrated embodiment, the antenna 200 includes a single tubular or annular fluid channel 210 that extends along a longitudinal axis 203 of the antenna 200. As shown, the fluid channel 210 can be formed in the dielectric insulator 204 and coaxially disposed around the inner conductor 202, with the dielectric insulator 204 separating the inner conductor 202 from the fluid channel 210. In other embodiments, the antenna 200 can include two separate channels that extend along opposite sides of the longitudinal axis 203 of the antenna 200, or any number of channels distributed around the circumference of the antenna 200. In addition, while the illustrated fluid channel 210 is formed through a portion of the dielectric insulator 204, in some embodiments the at least one fluid channel can be formed at another location (e.g., between the outer conductor 206 and shield 208, or on an outer surface of the antenna 200).

The at least one fluid channel can include at least one opening 212 to allow fluid to flow from within the channel into the tissue surrounding the antenna 200. The at least one opening 212 can extend through the outer edges of the antenna 200 to provide fluid communication between the at least one fluid channel and the tissue surrounding the antenna 200. The at least one opening 212 can be formed at any point along the length of the antenna 200, and the at least one fluid channel can similarly extend to any point along the length of the antenna 200. In some embodiments, for example, the at least one opening 212 can include a plurality of openings formed along a distal portion of the fluid channel 210 that terminates near the mid-point of the antenna 200, thereby introducing saline near a center of the microwave energy deposition pattern shown in FIG. 1. The plurality of openings can be formed in a variety of patterns, including, for example, in a pattern extending radially around the outer circumference of the antenna 200 or extending in symmetrically opposed lines along the longitudinal axis 203 of the antenna 200.

The at least one opening 212 can be formed in a variety of sizes, numbers, and pattern configurations. In addition, the at least one opening can be configured to direct fluid in a variety of directions with respect to the antenna 200. These can include the normal orientation (i.e., perpendicular to an antenna outer surface), as well as orientations directed proximally and distally along the longitudinal axis 203 of the antenna 200, including various orientations that develop a circular or spiral flow of liquid around the antenna. Still further, in some embodiments, the at least one fluid channel can extend to a distal end of the antenna 200 and the at least one opening 212 can be located on a distal surface of the antenna. A number of manufacturing methods are available to create the at least one opening, including, in one embodiment, creating one or more openings having a diameter of about 0.4 mm along a distal portion of fluid channel 210 using laser drilling.

In addition, the at least one fluid channel 210 can include a heating element disposed therein and configured to heat fluid flowing therethrough. Exemplary heating elements include, for example, assemblies that are configured to pass electrical energy through fluid within the channel between two or more electrodes. Exemplary designs for heating elements suitable for use with the microwave antenna 200 and other similar devices are described in U.S. Pat. Pub. No. 2012/0265190, which is hereby incorporated by reference in its entirety.

One skilled in the art will appreciate that the at least one fluid channel 210 and the at least one opening 212 can also be included in a number of other microwave antenna architectures in addition to the triaxial antenna 200. These can include, for example, slot, monopole, dipole, and choked microwave antenna architectures known in the art.

In use, fluid can be delivered into the tissue surrounding the antenna simultaneously with microwave energy from the antenna 200. The at least one opening 212 can be positioned such that the fluid is introduced into the tissue surrounding the antenna near the center of maximum heating and can flow through the extracellular space of the tissue to deliver a therapeutic dose of thermal energy. The fluid can carry significantly more energy deeper into the tissue because it carries the heat via convection.

By way of example, heat flowing in a given direction due to conduction is proportional to the thermal conductivity of the material k times the maximum temperature $T_{max}$ divided by the length scale a. By comparison, the heat carried by a flow of fluid Q in the same direction is proportional to the heat capacity of the fluid (e.g., saline) $p_f c_f$ times the maximum temperature $T_{max}$ times the flow velocity of the fluid $Q/4\pi a^2$. Therefore, the ratio of the amount of energy carried by convection to that carried by conduction can be expressed by the following equation:

$$\frac{\text{Convection}}{\text{Conduction}} \propto \frac{\rho_f c_f Q}{4\pi k a} \qquad (1)$$

This proportion calculates to about 11 for typical values of tissue thermal properties and for a flow rate of saline of about 10 ml/min and a microwave field that peaks at about 1 cm from the antenna. Thus, heat transfer into tissue is improved by an order of magnitude when saline is injected into tissue along with microwave energy.

Figure 3:
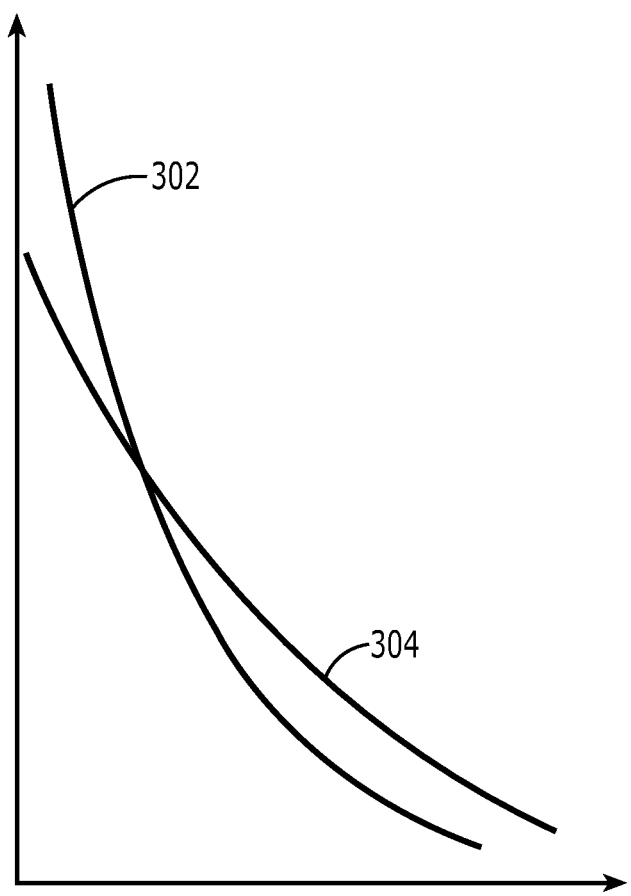
FIG. 3 is a graph showing microwave field strength and tissue temperature when saline flow is not present.

FIG. 3 illustrates an exemplary microwave power deposition profile 302 and tissue temperature profile 304 that can result from the use of the microwave antenna 200 without any fluid injection (i.e., similar to using the prior art antenna 100). While conduction does moderate the peak temperature from what would occur if the tissue were perfectly insulating (i.e., zero thermal conduction), the peak temperature remains near the location of peak power deposition, i.e., close to the antenna 200. Furthermore, both the power deposition level and tissue temperature fall off quickly with distance from the antenna.

Figure 4:
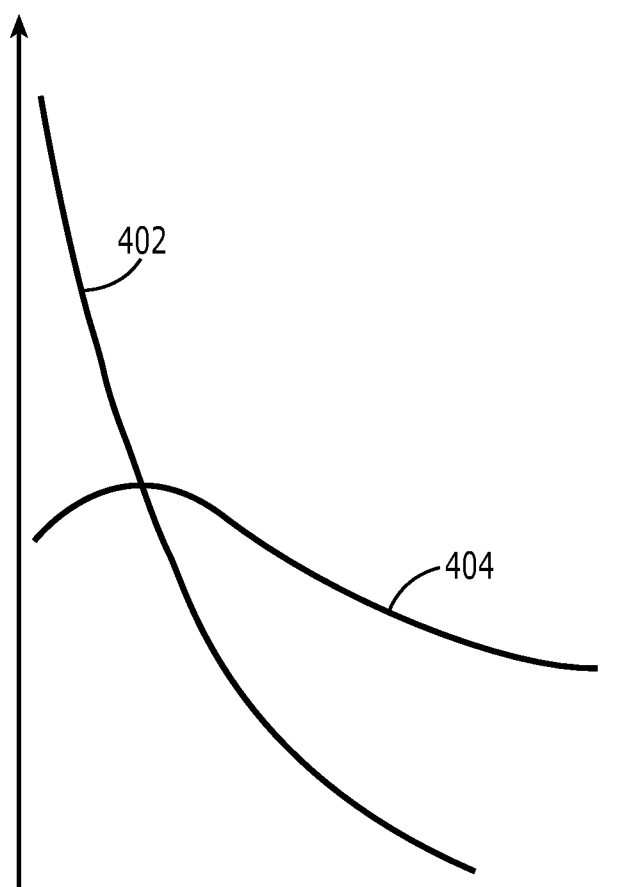
FIG. 4 is a graph showing microwave field strength and tissue temperature when saline flow is present.

In contrast, FIG. 4 illustrates an exemplary power deposition profile 402 and tissue temperature profile 404 that can result when the antenna 200 is used in combination with a 10 ml/min saline flow rate. As the figure shows, the temperature profile 404 is greatly modified. In particular, the peak temperature is reduced and the temperature profile becomes more uniform, resulting in a more uniform thermal dose being delivered across the treatment zone. Furthermore, the therapeutic temperatures (e.g., temperatures sufficiently high to destroy tissue) extend deeper into the tissue, resulting in more tissue being treated using a single antenna.

Figure 5:
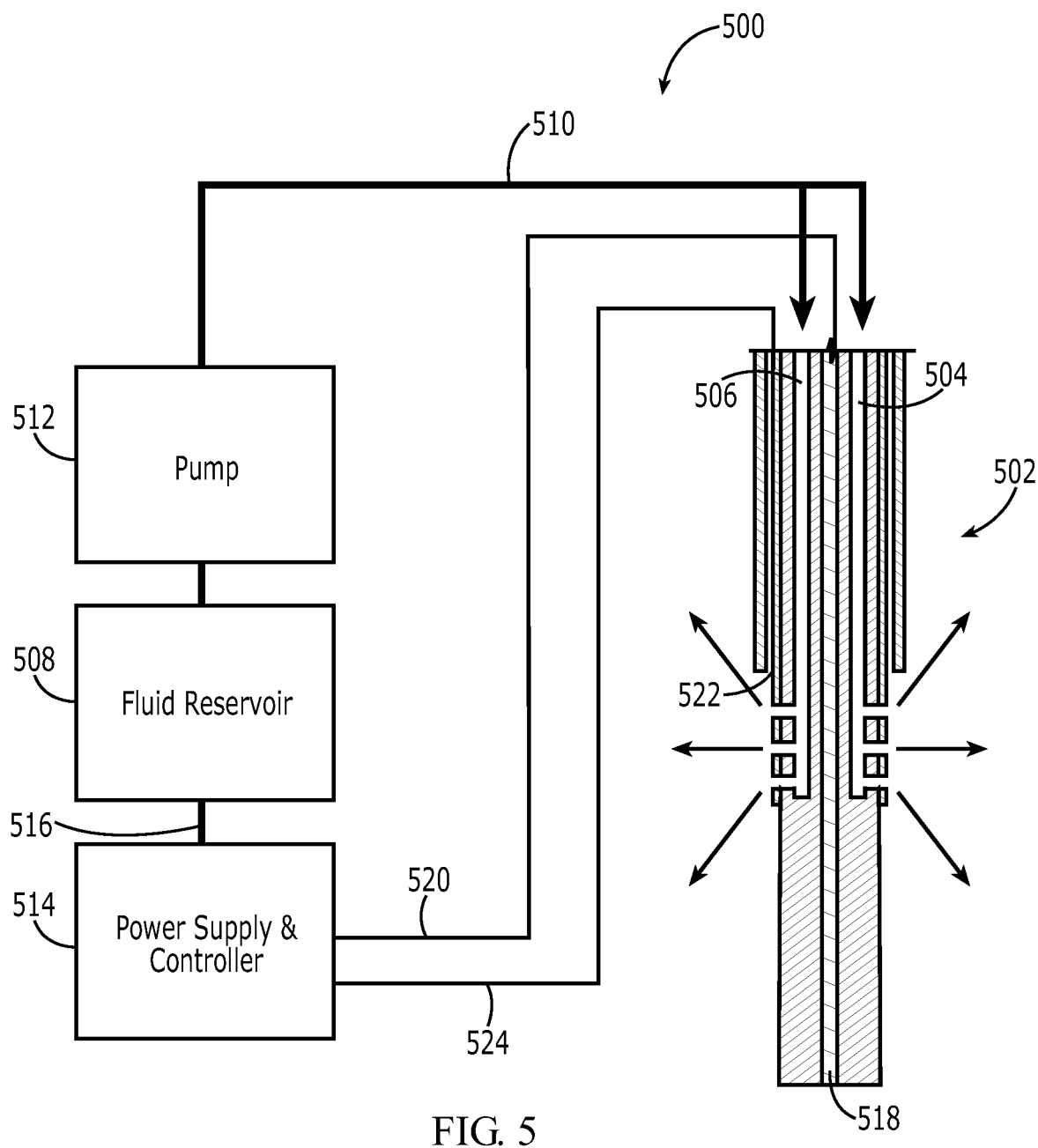
FIG. 5 is a diagram of one embodiment of a fluid enhanced ablation therapy system that includes a microwave antenna.

FIG. 5 illustrates one embodiment of a fluid enhanced ablation therapy system 500 that includes a microwave antenna 502 similar to the antenna 200 described above. The antenna 502 can have a variety of sizes according to the geometry of the target tissue, intended method for introduction into the target tissue, intended power output, etc. The antenna 502 can be configured for insertion into a target volume of tissue in a variety of manners, including, for example, laparoscopic percutaneous introduction or catheterization via a patient's circulatory system. In one embodiment, for example, the antenna 502 can be a probe between about 16- and 18-gauge (i.e., an outer diameter of about 1.27 mm to about 1.65 mm), and it can have a length that is approximately 20 cm. The antenna 502 can include a blunt distal end in some embodiments, or it can include a pointed distal tip configured to puncture tissue to facilitate introduction of the antenna 502 into a target volume of tissue.

The at least one fluid channel, such as the illustrated fluid channels 504, 506, can be coupled to a fluid reservoir 508 by at least one fluid conduit 510. The fluid conduit 510 can be, for example, a length of flexible plastic tubing. The fluid conduit 510 can also be a rigid tube, or a combination of rigid and flexible tubing. The fluid reservoir 508 can have a variety of geometries and sizes. In one embodiment, the fluid reservoir 508 can be a cylindrical container similar to a syringe barrel that can be used with a linear pump, as described below.

Fluid can be urged from the fluid reservoir 508 into the fluid channels 504, 506 of the antenna 502 by a pump 512. In one embodiment, the pump 512 can be a syringe-type pump that produces a fixed volume flow via linear advancement of a plunger (not shown). In other embodiments, however, other types of pumps, such as a diaphragm pump, may also be employed.

The pump 512, as well as any other components of the system, can be controlled by a controller 514. The controller 514 can include a power supply and can be configured to deliver electrical control signals to the pump 512 to cause the pump to produce a desired flow rate of fluid. The controller 514 can be connected to the pump 512 via an electrical connection 516. The controller 514 can also be electrically coupled to the antenna 502 using any known electrical connections of any desired length, though typically this connection is formed using a coaxial cable having an inner conductor and an outer conductor to mimic, for example, the structure of the antenna 200. Regardless of the physical form of the connection, an inner emitting conductor 518 of the antenna 502 can be electrically coupled to the power supply and controller 514 using an electrical connection 520. Similarly, an outer return conductor 522 can be coupled to the power supply and controller 514 using an electrical connection 524. In addition, the controller 118 can be connected to any heating assemblies disposed within the fluid channels 504, 506 (not shown) through a similar electrical connection.

In operation, the controller 514 can drive the delivery of fluid into target tissue at a desired flow rate, the heating of the fluid to a desired therapeutic temperature, and the delivery of microwave ablative energy via the antenna 502. To do so, the controller 514 can itself comprise a number of components for generating, regulating, and delivering required electrical control and therapeutic energy signals. In addition to the power supply mentioned above, the controller 514 can include one or more digital data processors and associated storage memories that can be configured to perform a variety of functions, or control discrete circuit elements that perform a given function. These functions can include, for example, the generation of one or more electrical signals of various frequencies and amplitudes. Furthermore, the controller 514 can be configured to amplify any of these signals using one or more power amplifiers. These amplified signals can be delivered to the antenna 502 via one or more electrical connections 520, passed through tissue surrounding the antenna 502, and returned to the power supply and controller 514 via the electrical connections 524. The controller 514 can also include a number of other components, such as a directional coupler to feed a portion of the one or more microwave signals to, for example, a power monitor to permit adjustment of the microwave signal power to a desired treatment level. Still further, the controller 514 can include a user interface to allow an operator to interact with the controller and set desired therapy operating parameters or receive feedback from the controller (e.g., warnings, indications, etc.).

Figure 6:
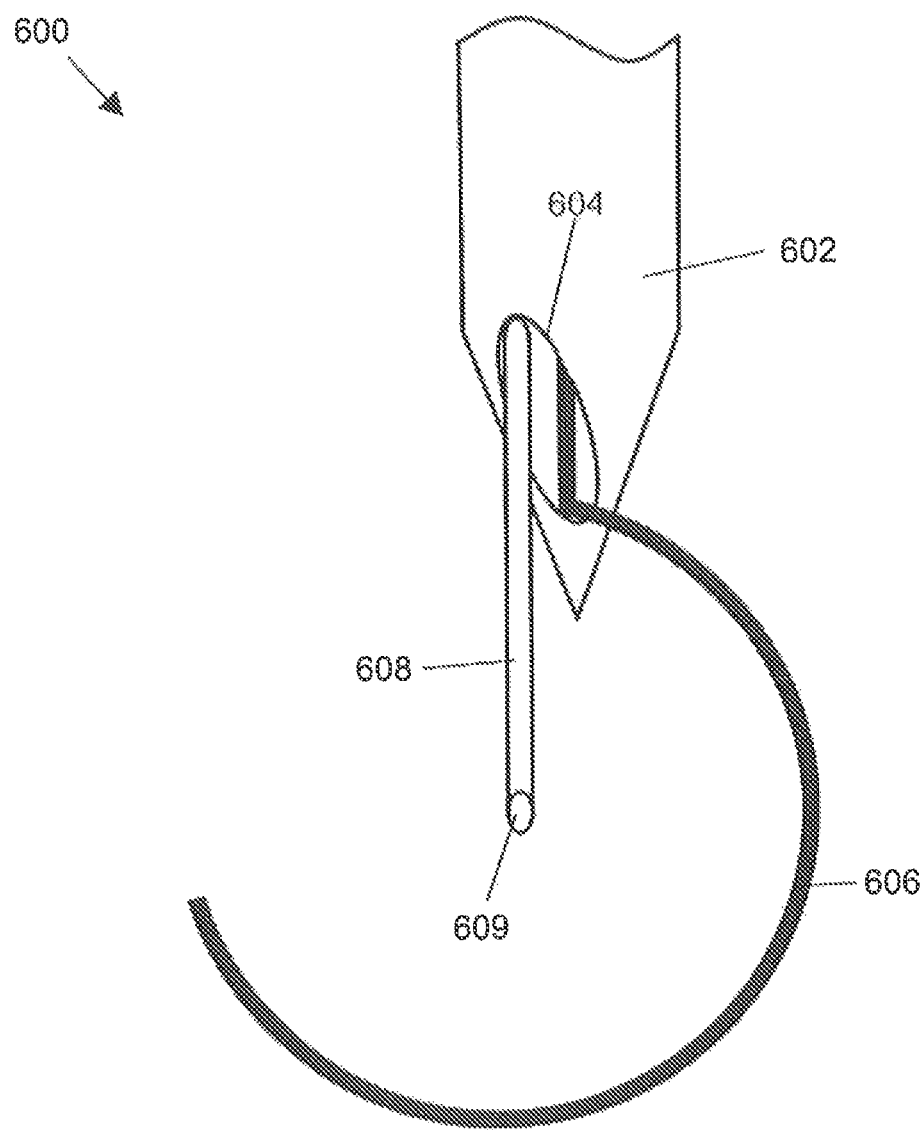
FIG. 6 is a diagram of an alternative embodiment of a microwave antenna.

As mentioned above, the triaxial antenna 200 is one of a variety of microwave antenna architectures known in the art. FIG. 6 illustrates an embodiment of a device 600 configured for use with a fluid enhanced ablation therapy system that utilizes a different embodiment of a microwave antenna. The device 600 can include an elongate body 602 having an inner lumen extending therethrough that is in communication with tissue surrounding the elongate body 602 via an opening 604 formed on a distal portion of the elongate body. An arced-shape microwave antenna 606 can be housed within the inner lumen and it can be configured to axially translate to extend through the opening 604 into the tissue surrounding the elongate body 602, as shown in the figure. The arced-shape antenna 606 can define a plane, i.e., it can trace a portion of a circle or other arc that lies within a plane (e.g., the plane of the page in FIG. 6). The arced-shape configuration of the antenna 606 can produce a roughly spherical microwave energy deposition field. An exemplary arced-shape antenna was formerly sold under the trade name VIVARING by Vivant/Valleylab.

Also housed within the inner lumen of the elongate body 602 can be a fluid passageway 608 having an opening formed at or near a distal end 609 thereof. Similar to the antenna 606, the fluid passageway 608 can be housed within the inner lumen of the elongate body 602 during insertion into a volume of tissue, and it can be configured to axially translate to extend from the opening 604 such that the distal end 609 is positioned at or near a center point of the arced-shape antenna 606, as shown in FIG. 6.

In use, fluid can be injected into the tissue surrounding the device 600 from the opening formed near the distal end 609 of the fluid passageway 608 at the same time that microwave energy is delivered into the tissue from the arc-shape antenna 606. The introduction of fluid at or near the center point of the arced-shape antenna is similar to the introduction of saline from the at least one opening 212 shown in FIG. 2. That is, saline or any other suitable fluid injected at this location acts as a point source, and the saline flows radially in a spherical pattern from the distal end of the fluid passageway 608. Such a source of saline can help the therapy temperature profile from microwave energy deposition grow in a spherical pattern.

Figure 7:
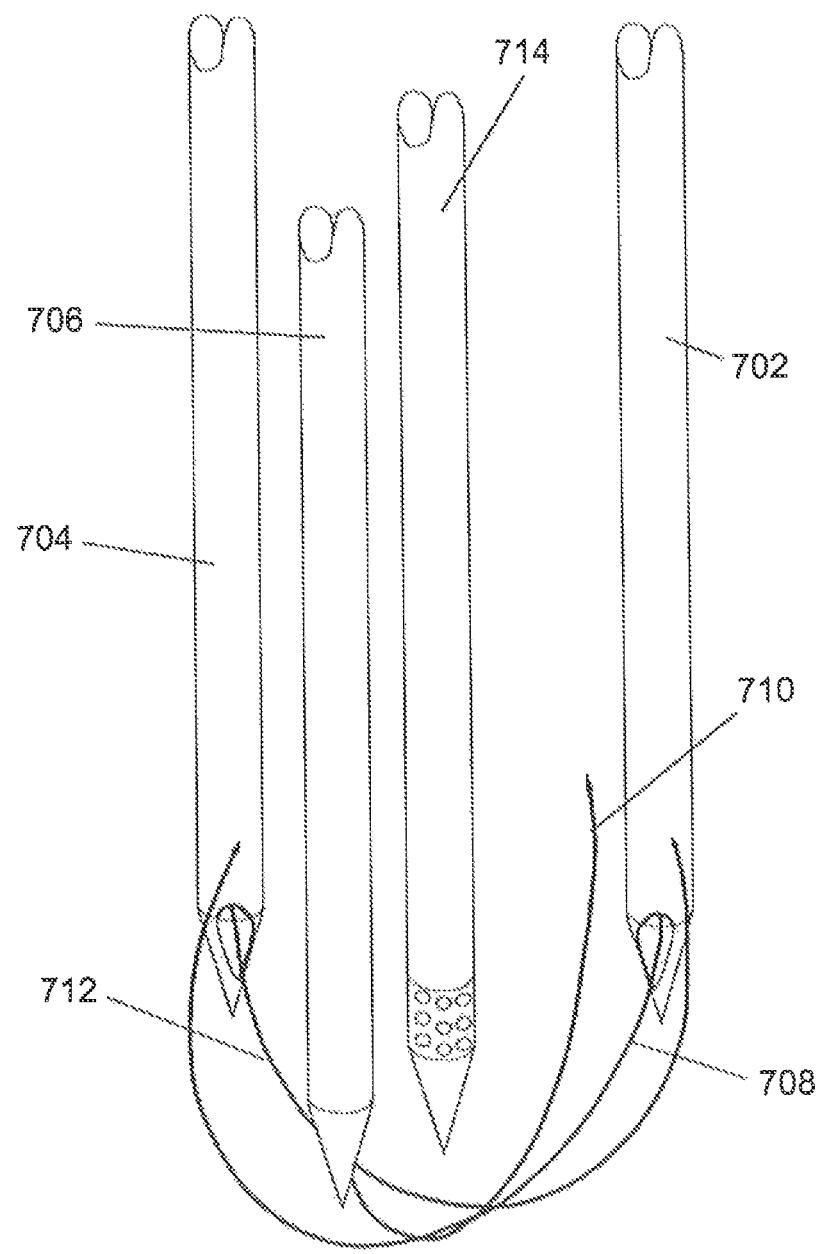
FIG. 7 is a diagram of another embodiment of a microwave antenna.

The device 600 can be used alone, as shown in FIG. 6, or it can be used in combination with one or more other devices to create a more spherical volume of therapeutically treated tissue. FIG. 7 illustrates one embodiment of an assembly that uses multiple arced-shape antennas to create such a pattern. In particular, three elongate bodies 702, 704, 706 can be positioned within a target volume of tissue such that their arced-shape microwave antennas 708, 710, 712 define planes that are angularly offset from one another and that intersect one another. In the illustrated embodiment, for example, the planes defined by the three microwave antennas 708, 710, 712 are each offset from one another by 120° such that they define three great circles (i.e., a circle on the surface of a sphere that lies in a plane passing through the sphere's center) of the spherical volume of tissue disposed between the antennas. In other embodiments, however, the antennas can be angularly offset by other amounts, including, for example, 90° (i.e., perpendicular orientation). Regardless, a fourth elongate body 714 can be introduced parallel to the elongate bodies 702, 704, 706 to introduce fluid into the target tissue volume. The elongate body 714 can be positioned vertically such that the fluid is introduced at or near the center of the sphere defined by the arced-shape microwave antennas 708, 710, 712.

Figure 8:
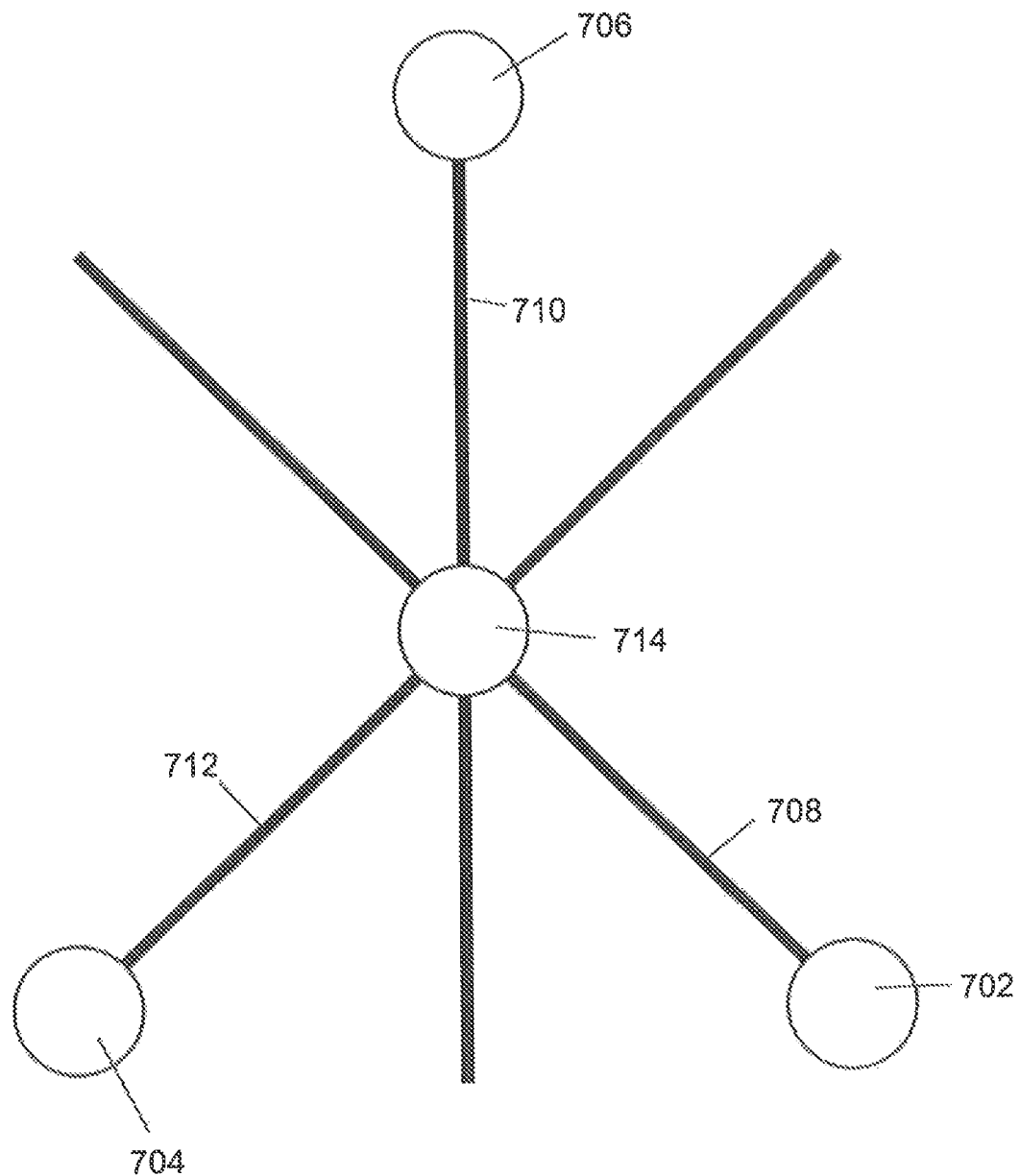
FIG. 8 is a top view of the microwave antenna of FIG. 7.

FIG. 8 shows a top view of the elongate bodies 702, 704, 706, 714, along with the arced-shape antennas 708, 710, 712. From this view, the angular offset of the planes defined by the antennas 708, 710, 712 and the central location of the elongate shaft 714 injecting fluid into the volume of tissue are visible. In such an embodiment, the flow of fluid from the elongate body 714 can be perpendicular to the energy deposition pattern and can moderate the peak temperatures, make the temperature in the therapy zone more uniform, and extend the heating field deeper into the tissue than is possible by using the antennas 708, 710, 712 alone.

Figure 9:
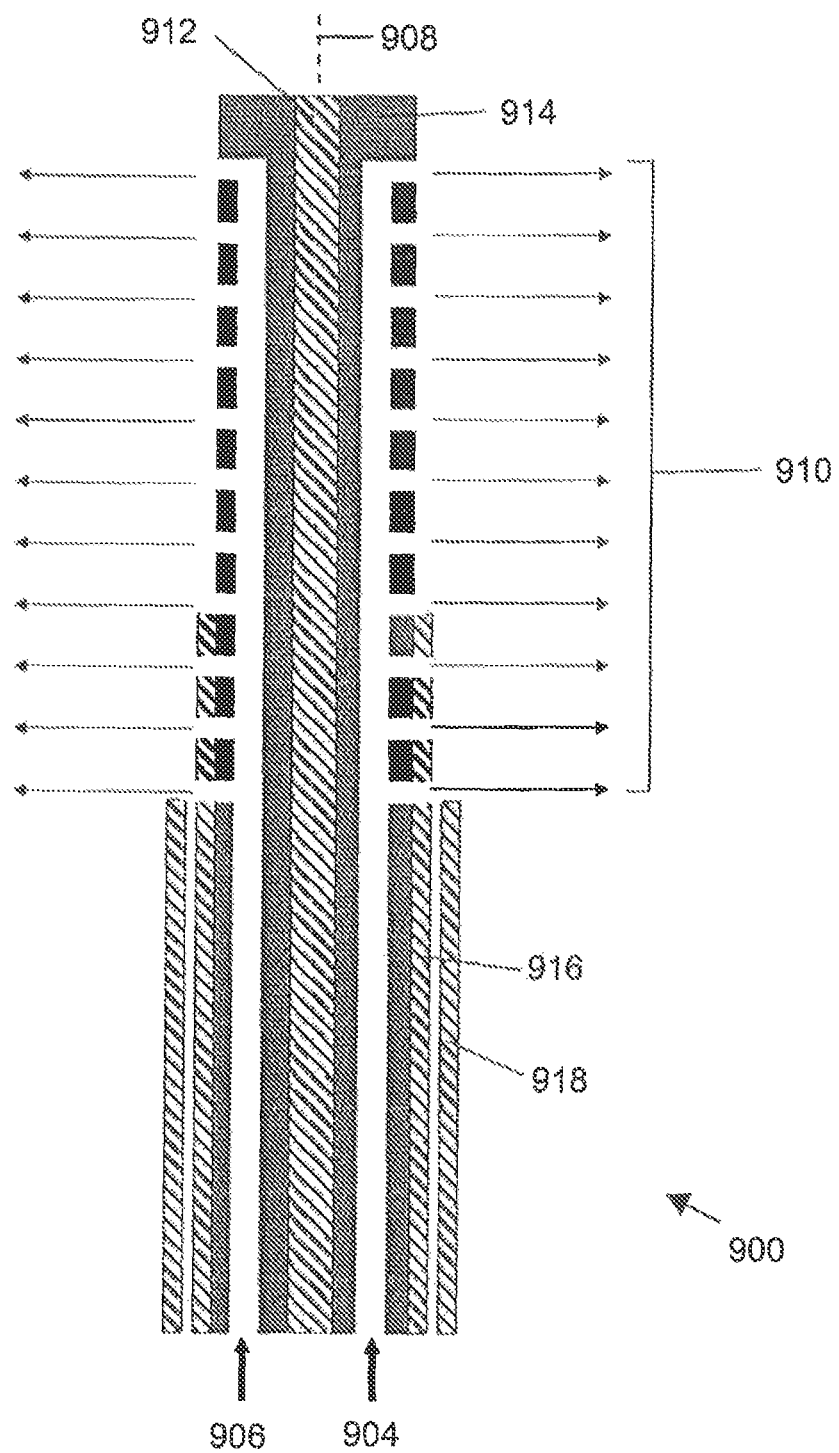
FIG. 9 is a cross-sectional diagram of an alternative embodiment of a microwave antenna.

Another alternative embodiment of a microwave antenna for use in fluid enhanced ablation therapy is shown in FIG. 9. The antenna 900 can include an inner conductor 912, a dielectric insulator 914, an outer conductor 916, and a shield 918 in a similar arrangement as antenna 200. In this embodiment, the microwave antenna 900 can also include dual fluid channels 904, 906 symmetrically disposed on opposing sides of a longitudinal axis 908 of the antenna. In an alternative embodiment, a single annular channel can be provided extending around the circumference of the antenna 900. Each fluid channel 904, 906 can include a plurality of linearly arranged openings 910 extending along the longitudinal axis 908 of the microwave antenna 900. In such an embodiment, the point saline source of FIG. 2 is extended by including the longer array of openings 910. As a result, this design can inject saline into the tissue as a line source, and the resultant saline flow within the target volume of tissue can be radially outward and cylindrically symmetric, rather than spherically symmetric as in the embodiment of FIG. 2. The resulting thermal field can be a substantially uniform temperature field extending cylindrically around the antenna 900.

Regardless of the antenna architecture used, in some embodiments, high fluid flow rates can provide too much cooling to the therapy. For example, the saline flow rate needed to effectively carry the heat delivered into the tissue can be significant, e.g., as high as 50 ml/min or more. Saline flow into the tissue at such rates can substantially quench the thermal therapy, keeping the tissue below a therapeutic temperature. To combat this problem, or to impart additional energy into the tissue even at lower fluid flow rates, the saline or other suitable fluid can be heated to a therapeutic temperature prior to being introduced into the target volume of tissue.

Figure 10:
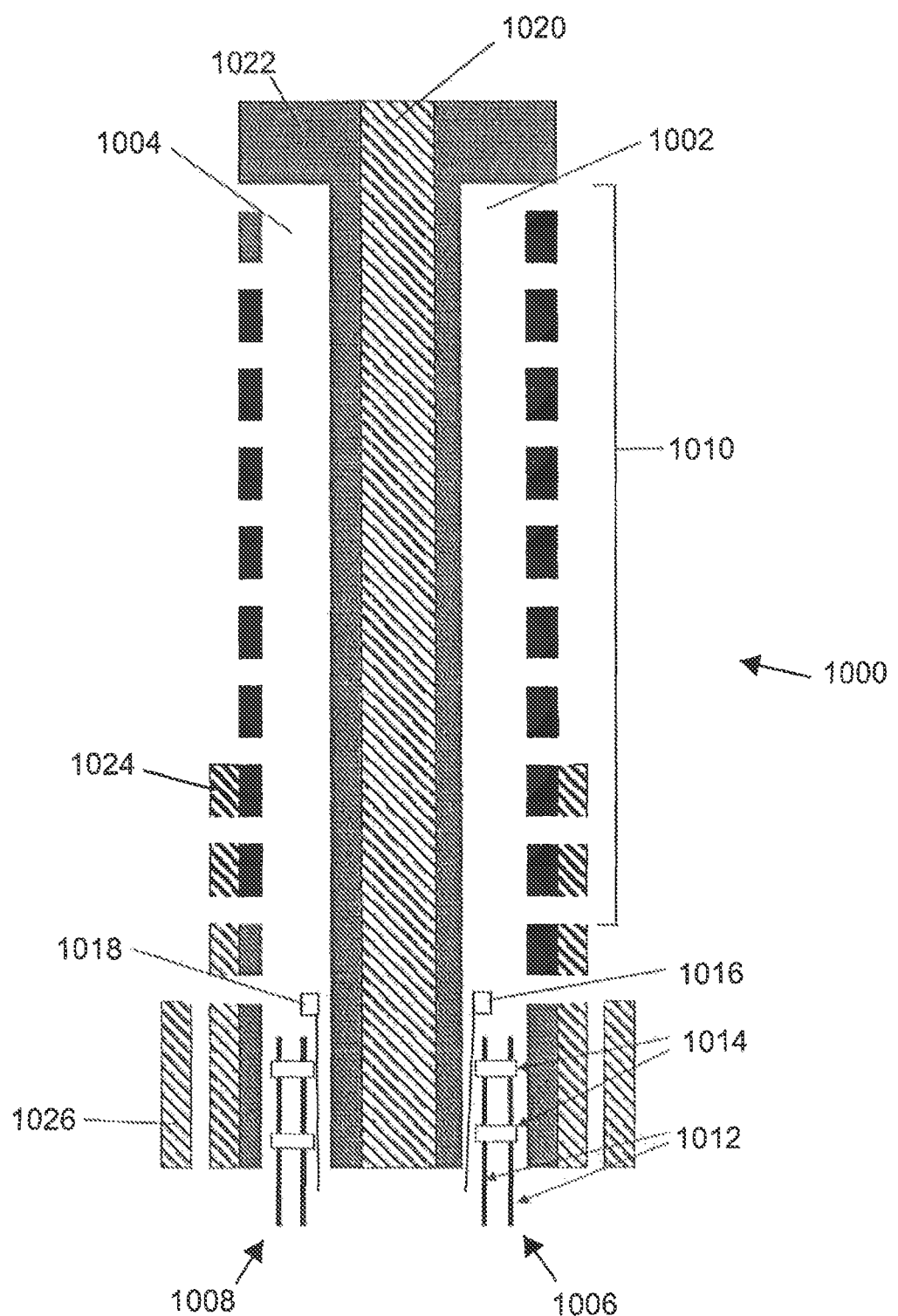
FIG. 10 is a cross-sectional diagram of yet another embodiment of a microwave antenna.

FIG. 10 illustrates one embodiment of a microwave antenna 1000 that is similar to the triaxial fluid enhanced ablation antenna 900 described above. It similarly includes an inner conductor 1020, dielectric insulator 1022, outer conductor 1024, and shield 1026 arranged in the same configuration. The antenna can also include at least one fluid channel, such as dual fluid channels 1002, 1004. However, each of the fluid channels in this exemplary embodiment can further include at least one heating element disposed therein. In the illustrated embodiment, for example, the heating elements 1006, 1008 are disposed in the two fluid channels 1002, 1004, respectively. The heating elements can be used to heat fluid flowing through the fluid channels 1002, 1004 prior to their introduction into tissue surrounding the antenna 1000 via a plurality of openings 1010 formed in each of the fluid channels.

The heating elements 1006, 1008 can have a variety of forms but, in some embodiments, can be dual-wire electrical heating assemblies that pass RF electrical energy between two wires 1012 to heat the fluid. The wires can be insulated along a proximal portion thereof extending from a power source, as described above. The wires 1012 can be exposed along a distal portion thereof to allow the passage of energy therebetween, and electrical shorts can be prevented by non-conducting spacers 1014 that hold the wires 1012 apart from one another. A thermocouple 1016, 1018 or other temperature monitoring element can also be disposed within the fluid channels 1002, 1004 to aid an operator or control system in regulating the power applied to the heating elements 1006, 1008 to achieve the desired temperature of fluid prior to introduction into tissue. Exemplary embodiments of the dual-wire heating elements 1006, 1008 are described in U.S. Pat. Pub. No. 2012/0265190, which is incorporated by reference above.

In addition to the dual-wire heating elements described above, alternative forms of heating elements can also be suitable for use with the devices and methods described herein. For example, instead of using two separated wires, a heating element can utilize any two or more metal electrodes in contact with the saline or other suitable fluid that can pass electrical current, thereby heating the saline resistively. Another embodiment described in U.S. Pat. Pub. No. 2012/0265190, incorporated by reference above, utilizes a single wire disposed within a fluid channel formed of an electrically conductive material. As a result, the fluid channel itself acts as the second electrode in combination with the single wire disposed within the channel. Similar to the dual-wire heating element described above, a non-conducting spacer element can be utilized to prevent electrical shorts between the single wire and the conductive walls of the fluid channel.

In still other embodiments, a heating element can be a high-frequency microwave antenna whose frequency is selected such that the energy field it generates is fully dissipated within the fluid channel. Similarly, a heating element can employ an electrically resistive material in contact with the saline that is heated via electrical power such that the resulting dissipated energy can be passed into the saline through thermal conduction.

In certain microwave antenna architectures known in the art, a cryogenic gas has been used to control internal heating of a proximal portion of a microwave antenna and the cabling connecting the antenna to a power source. One such embodiment of a cryogenically cooled microwave ablation system is described in U.S. Pat. No. 7,244,254, which is hereby incorporated by reference in its entirety. As described in that reference, heating of a cable and the proximal portion of a microwave antenna coupled thereto can be controlled by the use of a cooled gas, ideally a cryogenic gas that can exceptionally cool when expanded due to the Joule-Thompson effect. In use, a cryogenic gas is introduced into an internal gas feed line disposed along the length of the power supply cable. The gas travels through the feed line toward the proximal end of the antenna and is allowed to expand as it reaches the antenna. The expansion of the gas near the proximal end of the antenna can effectively cool that portion of the antenna, and the gas can subsequently be routed to a vent along a proximal portion of the cable.

Figure 11:
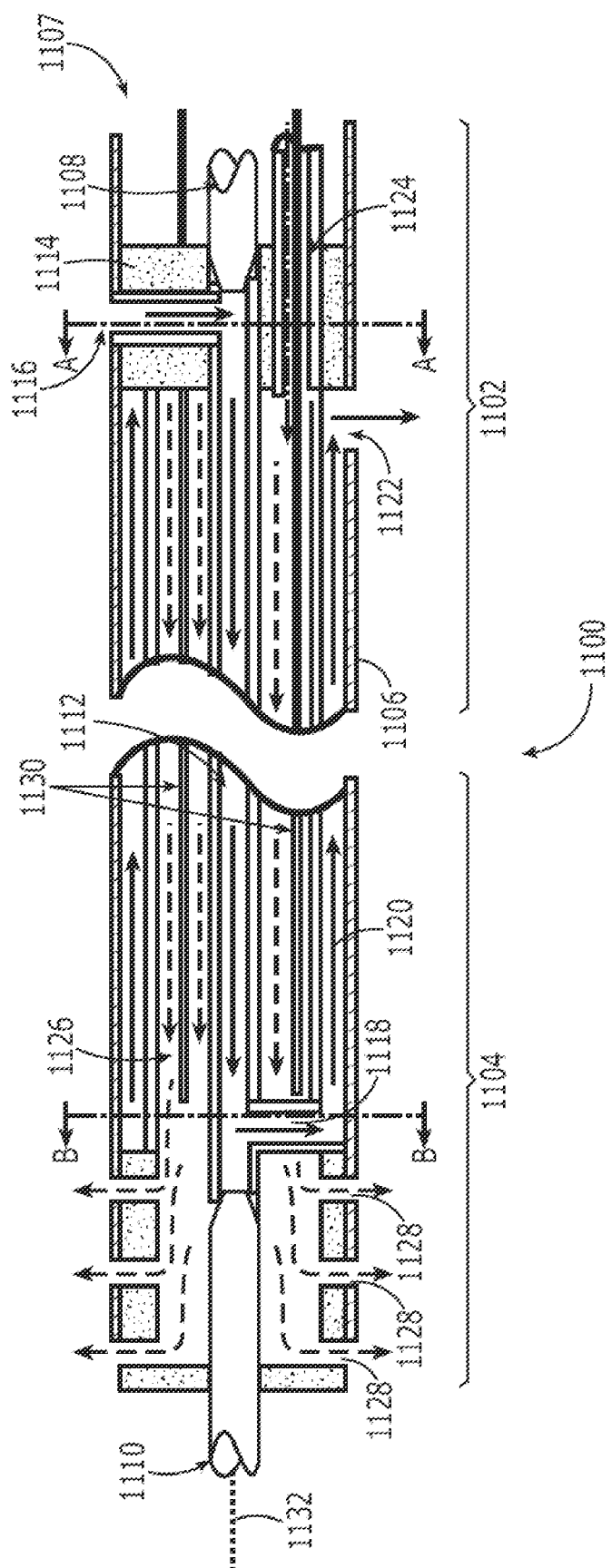
FIG. 11 is a cross-sectional diagram of one embodiment of a microwave antenna assembly.
Figure 12:
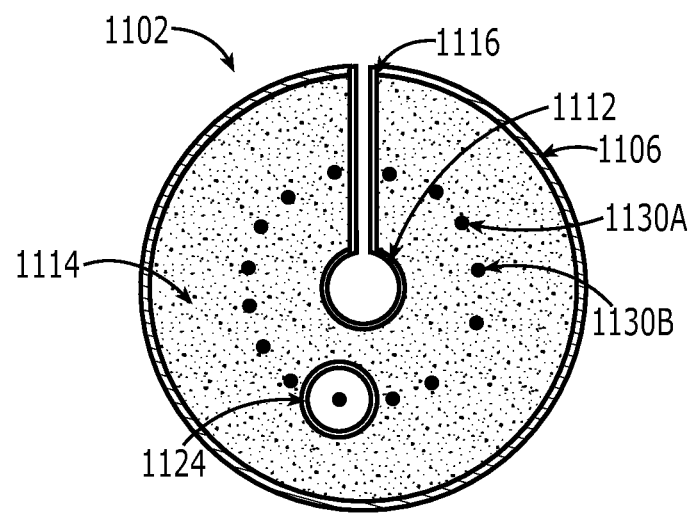
FIG. 12 is a cross-sectional diagram of the microwave antenna assembly of FIG. 11 at location A-A.
Figure 13:
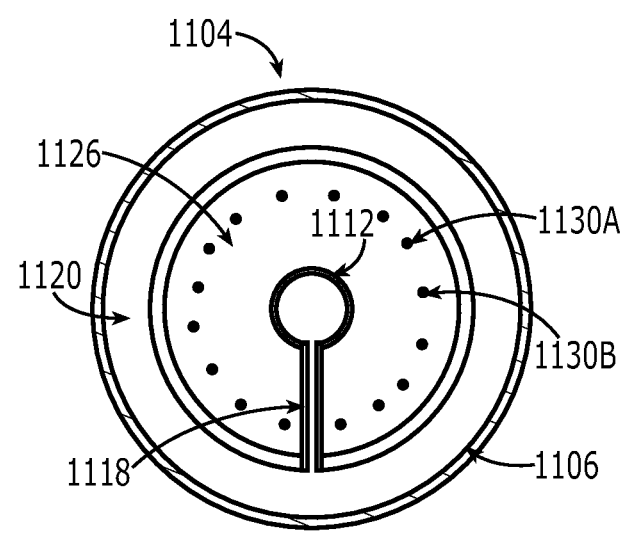
FIG. 13 is a cross-sectional diagram of the microwave antenna assembly of FIG. 11 at location B-B.

This design can provide adequate cooling of the cable and antenna, but does not remedy the challenges encountered with conventional microwave ablation related to treating larger volumes of tissue, as explained above. FIGS. 11-13 illustrate one embodiment of a cryogenically cooled microwave antenna assembly configured for use with fluid enhanced ablation therapy.

With reference to FIG. 11, a microwave antenna assembly 1100 is shown that includes a microwave power cable 1102 and an antenna 1104. The illustrated antenna 1104 can be a monopole or dipole antenna, but the principles of the invention can be applied to other microwave antenna architectures as well. As shown in the figure, an outer return conductor 1106 can extend along an outer surface of the antenna assembly 1100 from the antenna 1104 to the cable 1102 and ultimately to a power supply, such as the power supply and controller 514 discussed above. The outer return conductor 1106 can define an inner lumen 1107, and an inner emitting conductor 1108 can be disposed within the inner lumen 1107 in a proximal portion of the cable 1102. A similar inner emitting conductor 1110 can be disposed in a distal portion of the antenna 1110. The inner conductors 1108, 1110 can be coupled by an inner gas feed line 1112 that extends along the length of a distal portion of the cable 1102 and a proximal portion of the antenna 1104. The gas feed line 1112 can be formed from a metal tube so that it can effectively conduct microwave power from inner emitting conductor 1108 to inner emitting conductor 1110.

A proximal portion of the power cable 1102 can also include a solid structural support 1114 disposed therein and filling the inner lumen 1107. The outer return conductor 1106 and the structural support 1114 can have a gas supply inlet 1116 extending therethrough that is in fluid communication with the gas feed line 1112. The gas supply inlet 1116 can be, for example, a radially-oriented tube that passes through the outer return conductor 1106 and the solid structural support 1114.

Cryogenic gas that enters the gas supply inlet 1116 can be carried forward toward the proximal end of the antenna 1104 within the gas feed line 1112. Upon reaching the proximal end of the antenna 1104, the cryogenic gas can be allowed to expand by passing through a gas expansion conduit 1118 into an annular-shape gas return conduit 1120 that is disposed around an outer circumference of the inner lumen 1107. The cryogenic gas can provide additional cooling as it expands into the larger annular gas return conduit 1120 due to the Joule-Thompson effect. The expanded gas can then be carried back toward the proximal end of the cable 1102 to be expelled through a gas vent 1122.

In addition to the various gas supply lines, the inner lumen 1107 can also house fluid supply lines configured to carry fluid from a source connected to the proximal end of the cable 1102 to the antenna 1104. For example, in some embodiments a fluid supply line 1124 can extend from a proximal end of the cable 1102 through the structural support 1114. After passing through the structural support 1114, the fluid supply line can, in some embodiments, expand to fill the annular conduit 1126 that extends along the distal portion of the cable 1102 and the proximal portion of the antenna 1104 between the outer wall of the gas feed line 1112 and the inner wall of the gas return conduit 1120. Once the flowing fluid reaches the distal end of the antenna 1104, it can be injected into tissue surrounding the antenna via at least one opening, e.g., a plurality of radially oriented openings 1128 formed in the antenna 1104 (similar to the operation of the antenna 200 described above). The introduction of fluid into the tissue can aid in delivering thermal energy deeper into the tissue than is possible with microwave ablation alone.

The fluid, typically saline, is in good thermal communication with the returning cooled gas in the gas return conduit 1120. As a result, the fluid can be cooled as it travels along the length of the cable 1102 and antenna 1104. Indeed, in some embodiments, the fluid can be cooled to below body temperature prior to being injected into tissue. In the event that this is not desirable, one or more heating elements can be placed within the annular conduit 1126 to heat the fluid flowing therethrough. In the illustrated embodiment, for example, two or more RF electrodes 1130 can be oriented along a longitudinal axis 1132 of the fluid annular conduit 1126 for fluid supply conduit 1124. The electrodes 1130 can be passed through the structural support 1114 to reach a power supply at a proximal end of the cable 1102 and, if more than two are used, emitting electrodes can be alternated with return electrodes, as shown by emitter electrodes 1130A and return electrodes 1130B in FIGS. 12 and 13.

The one or more heating elements disposed within the inner lumen 1107 can be used to heat the fluid flowing therethrough to any desired temperature. A temperature sensor (not shown) can be positioned in the antenna 1104 proximal to the openings 1128 to detect the temperature of the fluid being injected into the tissue surrounding the antenna 1104. This feedback can be used to control the amount of energy applied to the heating elements and achieve a desired temperature for the fluid upon injection into tissue.

Furthermore, as a result of the fact that the fluid can be cooled significantly by the cryogenic gas, any desired temperature between the solid phase change temperature and the gas phase change temperature (e.g., approximately 0° C. and 100° C., respectively, for saline) can be achieved by balancing the amount of cooling gas provided and the RF energy applied to the one or more electrodes 1130. This provides a novel benefit over prior art solutions, as it has not previously been possible to introduce fluid into the tissue at a temperature below at least room temperature, if not body temperature.

FIG. 12 shows a cross-sectional view of the cable 1102 at location A-A shown in FIG. 11. Visible in the figure are the outer return conductor 1106, gas feed line 1112, solid structural support 1114, gas supply inlet 1116, fluid supply line 1124, RF emitter electrodes 1130A, and RF return electrodes 1130B (extending in alternating pairs around the circumference of the inner lumen 1107).

FIG. 13 similarly shows a cross-sectional view of the antenna 1104 at location B-B shown in FIG. 11. Visible in this figure are the outer return conductor 1106, gas feed line 1112, gas expansion conduit 1118, annular gas return conduit 1120, annular conduit 1126, RF emitter electrodes 1130A, and RF return electrodes 1130B (again shown extending in alternating pairs around the circumference of the inner lumen 1107).

Those skilled in the art will appreciate that a number of variations are possible on the embodiment shown in FIGS. 11-13. For example, a number of alternative heating elements can be employed in place of the RF electrodes, such as laser-based heaters, resistive heaters, etc. Furthermore, there can be more than one heating element disposed along the length of the assembly 1100. For example, one or more proximal heating elements can be positioned near a proximal end of the cable 1102 and used to control the temperature of a fluid prior to entering a second, more distal set of one of more heating elements. This second set of heating elements can, for example, be positioned just proximal to the plurality of openings 1128 and used to control the temperature of the fluid prior to injection into tissue surrounding the antenna 1104. In this manner, the temperature of the microwave cable and antenna proximal to the therapy zone can be controlled by the first, proximal set of heating elements to be at a sub-therapeutic temperature (e.g., typically 41° C. or cooler to avoid destroying tissue) and a second, more distal set of heating elements can be used to further raise the temperature to a therapeutic level (e.g., above 41° C.).

Accordingly, methods according to the teachings of the present invention can include, for example, delivering therapeutic energy through a microwave antenna configured to be positioned within a volume of tissue, while simultaneously delivering heated fluid into the volume of tissue through at least one outlet port formed in the microwave antenna. In certain embodiments, the fluid can be heated solely by contacting the microwave antenna and drawing excess heat therefrom. In other embodiments, however, the excess heat from the microwave antenna may not heat the fluid to a desired therapeutic temperature. In such an embodiment, one or more heating elements disposed within the microwave antenna (e.g., within a fluid passageway formed in the antenna) can be used to raise the temperature of the heated fluid prior to its introduction into tissue surrounding the antenna.

In other embodiments, a method for ablating tissue according to the teachings of the present invention can include delivering therapeutic energy into a volume of tissue using a microwave antenna, and cooling the microwave antenna by delivering a cryogenic gas through at least one gas channel formed in the microwave antenna. The method can further include delivering a fluid into the volume of tissue through at least one fluid channel formed in the microwave antenna, and controlling the temperature of the fluid delivered into the volume of tissue using the cooling of the cryogenic gas and one or more heating elements disposed within the at least one fluid channel. As mentioned above, by balancing the cooling effects of the cryogenic gas with the output of the one or more heating elements, the fluid can be controlled to enter the tissue surrounding the antenna at any temperature between, e.g., a freezing and a boiling temperature of the fluid.

Any devices disclosed herein can be designed to be disposed after a single use, or they can be designed for multiple uses. In either case, however, the devices can be reconditioned for reuse after at least one use. Reconditioning can include any combination of the steps of disassembly of a device, followed by cleaning or replacement of particular pieces, and subsequent reassembly. In particular, a device can be disassembled, and any number of the particular pieces or parts of the device can be selectively replaced or removed in any combination. Upon cleaning and/or replacement of particular parts, a device can be reassembled for subsequent use either at a reconditioning facility or by a surgical team immediately prior to a surgical procedure. Those skilled in the art will appreciate that the reconditioning of a device can utilize a variety of techniques for disassembly, cleaning/replacement, and reassembly. Use of such techniques, and the resulting reconditioned device, are all within the scope of the present invention.

Preferably, any devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other sterilization techniques can include beta radiation, ethylene oxide, steam, and a liquid bath (e.g., cold soak). In certain embodiments, the materials selected for use in forming certain components may not be able to withstand certain forms of sterilization, such as gamma radiation. In such a case, suitable alternative forms of sterilization can be used, such as ethylene oxide.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:
1. A microwave ablation device, comprising:
an elongate body having
  an inner conducting element surrounded by a dielectric insulator,
  an outer conducting element coaxially disposed around the dielectric insulator and defining an outer wall, and
  a plurality of separate fluid channels extending through the dielectric insulator parallel to a longitudinal axis of the microwave antenna, each fluid channel including at least one opening positioned proximal to a distal end of the outer conducting element and extending through the dielectric insulator and the outer conducting element to allow fluid to flow into tissue surrounding the elongate body;

wherein the inner and outer conducting elements are configured to deliver microwave energy to tissue surrounding the elongate body, the dielectric insulator extends distally beyond the distal end of the outer conducting element, and each fluid channel terminates at a location proximal to a distal end of the dielectric insulator.

2. The device of claim 1, wherein the at least one opening comprises a plurality of openings spaced along a longitudinal axis of each of the plurality of fluid channels.

3. The device of claim 1, wherein the at least one opening comprises a plurality of openings spaced circumferentially around a longitudinal axis of each of the plurality of fluid channels.

4. The device of claim 1, wherein the microwave antenna has a cylindrical shape, and wherein the inner conducting element, dielectric insulator, and outer conducting element are coaxially aligned.

5. The device of claim 1, wherein each of the plurality of fluid channels, includes a heating element disposed therein, the heating element being positioned proximal to the at least one opening and configured to heat fluid flowing through the channel.

6. The device of claim 1, further comprising a shield disposed around and coaxially aligned with the outer conducting element.

7. The device of claim 1, wherein the distal end of the dielectric insulator is positioned at a distal end of the inner conductor.

8. An ablation device, comprising:
a microwave antenna having
a hollow outer conducting element,
a coaxial inner conducting element extending through the outer conducting element,
an annular fluid channel surrounding the inner conducting element,
an inner lumen extending through the inner conducting element,
an annular return channel in fluid communication with the inner lumen, isolated from the fluid channel, and positioned between the fluid channel and the outer conductor; and
at least one outlet port formed in the outer conducting element at a distal end of the antenna and in fluid communication with the fluid channel, the at least one outlet port being configured to deliver fluid flowing through the fluid channel into tissue surrounding the microwave antenna;
wherein the inner lumen is configured to receive a cryogenic gas and vent the cryogenic gas into the return channel such that the cryogenic gas does not enter the fluid channel.

9. The device of claim 8, further comprising at least one heating element disposed in the fluid channel and configured to heat fluid flowing through the channel.

10. The device of claim 8, wherein the at least one outlet port formed in the outer conducting element is positioned distally of a distal end of the return channel.

* * * * *